United States Patent
Govari et al.

(10) Patent No.: US 11,642,481 B2
(45) Date of Patent: May 9, 2023

(54) PATIENT VENTILATION SYSTEM HAVING SENSORS AND ELECTRODES COUPLED TO INTUBATIONS TUBE

(71) Applicant: Biosense Webster (Israel) Ltd., Yokneam (IL)

(72) Inventors: Assaf Govari, Haifa (IL); Yehuda Algawi, Binyamina (IL); Eran Aharon, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 383 days.

(21) Appl. No.: 17/131,953

(22) Filed: Dec. 23, 2020

(65) Prior Publication Data

US 2022/0193353 A1    Jun. 23, 2022

(51) Int. Cl.
*A61M 16/00* (2006.01)
*A61M 16/04* (2006.01)
*A61M 16/16* (2006.01)
*A61N 1/05* (2006.01)
(Continued)

(52) U.S. Cl.
CPC ...... *A61M 16/024* (2017.08); *A61M 16/0057* (2013.01); *A61M 16/04* (2013.01);
(Continued)

(58) Field of Classification Search
CPC .. A61M 16/00; A61M 16/0057; A61M 16/01; A61M 16/024; A61M 16/04;
(Continued)

(56) References Cited

U.S. PATENT DOCUMENTS 6,587,726 B2    7/2003  Lurie et al.
7,747,319 B2    6/2010  Freeman
(Continued)

FOREIGN PATENT DOCUMENTS

WO    200132249 A1    10/2001
WO    2009042973 A1    4/2009
(Continued)

OTHER PUBLICATIONS

EP Application No. 21217003.9-1122—Extended European Search Report dated May 23, 2022.

*Primary Examiner* — Joseph D. Boecker
(74) *Attorney, Agent, or Firm* — Louis J. Capezzuto (57) ABSTRACT

A ventilator system for a patient includes: an intubation tube configured to flow oxygen-enriched humidified air (OHA) toward patient lungs and to evacuate exhaust air exhaled from the lungs, the intubation tube includes: a distal end, configured to be inserted into patient trachea, and a proximal end, configured to be connected to tubes for receiving the OHA and evacuating the exhaust air; a first microgravity sensor, coupled to the intubation tube at a first position, and configured to produce a first signal indicative of a first micro-acceleration of the intubation tube at the first position; a second microgravity sensor, coupled to the intubation tube at a second different position, and configured to produce a second signal indicative of a second micro-acceleration of the intubation tube at the second position; and a processor, configured to control the ventilation system to apply a ventilation scheme responsively to the first and second signals.

20 Claims, 2 Drawing Sheets

(51) Int. Cl.
*A61N 1/36* (2006.01)
*A61M 16/12* (2006.01)

(52) U.S. Cl.
CPC ........ *A61M 16/0402* (2014.02); *A61M 16/16* (2013.01); *A61N 1/0519* (2013.01); *A61N 1/3601* (2013.01); *A61M 16/12* (2013.01); *A61M 2016/0027* (2013.01); *A61M 2202/0208* (2013.01); *A61M 2205/3327* (2013.01); *A61M 2205/50* (2013.01); *A61M 2210/1032* (2013.01); *A61M 2230/432* (2013.01)

(58) Field of Classification Search
CPC .......... A61M 16/0402; A61M 16/1005; A61M 16/12; A61M 16/16; A61M 2230/63; A61N 1/0519
See application file for complete search history.

(56) References Cited

U.S. PATENT DOCUMENTS

| | | |
|---|---|---|
| 8,651,105 B2 | 2/2014 | Christopher et al. |
| 8,776,793 B2 | 7/2014 | Wondka et al. |
| 9,339,208 B2 | 5/2016 | Wood et al. |
| 2009/0151719 A1* | 6/2009 | Wondka .............. A61M 16/024 128/204.23 |
| 2010/0163023 A1* | 7/2010 | Singh ................. A61M 16/044 73/1.01 |
| 2011/0190596 A1* | 8/2011 | Hacker .................. A61B 5/394 600/301 |
| 2013/0184567 A1* | 7/2013 | Xie ........................ A61B 5/065 600/595 |
| 2013/0269701 A1 | 10/2013 | Lurie |
| 2014/0180138 A1* | 6/2014 | Freeman .............. A61B 5/0809 600/536 |
| 2015/0265790 A1* | 9/2015 | Nolan ............... A61M 16/0486 128/202.16 |
| 2019/0224434 A1* | 7/2019 | Silver .................... A61H 31/00 |
| 2019/0232004 A1* | 8/2019 | Conrad ............... A61M 16/022 |
| 2021/0316098 A1* | 10/2021 | Van Wolferen ........ A61B 5/682 |

FOREIGN PATENT DOCUMENTS

| | | |
|---|---|---|
| WO | 2015143452 A1 | 9/2015 |
| WO | 2018031784 A1 | 2/2018 |

* cited by examiner

PATIENT VENTILATION SYSTEM HAVING SENSORS AND ELECTRODES COUPLED TO INTUBATIONS TUBE

FIELD OF THE INVENTION

The present invention relates generally to ventilation systems of patients, and particularly to methods and systems for improving ventilation of a patient using sensors coupled to an intubation tube of a ventilation system.

BACKGROUND OF THE INVENTION

Various techniques for estimating respiratory status of a patient and adjusting ventilation scheme have been published in the patent literature.

For example, U.S. Pat. No. 6,587,726 describes exemplary devices and methods for electrically stimulating the phrenic nerve. In one embodiment, electrodes are placed posterior and anterior in the region of the cervical vertebrae. Electrical current having a multi-phasic waveform is periodically applied to the electrodes to stimulate the phrenic nerve, thereby causing the diaphragm to contract.

U.S. Patent Application Publication 2013/0269701 describes a medical method for treating a person and comprises repeatedly compressing the person's chest. While repeatedly compressing the person's chest, the method further includes repeatedly delivering a positive pressure breath to the person and extracting respiratory gases from the person's airway using a vacuum following the positive pressure breath to create an intrathoracic vacuum to lower pressures in the thorax and to enhance blood flow back to the heart.

SUMMARY OF THE INVENTION

An embodiment of the present invention that is described herein provides a ventilator system for a patient, the ventilator system includes an intubation tube, first and second microgravity sensors, and a processor.

The intubation tube is configured to flow oxygen-enriched humidified air (OHA) toward lungs of the patient and to evacuate exhaust air exhaled from the lungs, the intubation tube including: (i) a distal end, configured to be inserted into a trachea of the patient, and (ii) a proximal end, configured to be connected to one or more tubes for receiving the OHA and evacuating the exhaust air. The first microgravity sensor is coupled to the intubation tube at a first position, and is configured to produce a first signal indicative of a first micro-acceleration of the intubation tube at the first position. The second microgravity sensor is coupled to the intubation tube at a second position, different from the first position, and is configured to produce a second signal indicative of a second micro-acceleration of the intubation tube at the second position. The processor is configured to control the ventilation system to apply a ventilation scheme responsively to the first and second signals.

In some embodiments, the processor is configured to estimate a respiratory status of the patient based on the first and second signals, and to control the ventilation system to apply the ventilation scheme depending on the estimated respiratory status. In other embodiments, the processor is configured to calculate, based on the first and second signals, a differential signal for estimating the respiratory status of the patient. In yet other embodiments, the ventilation system includes one or more additional sensors, which are coupled to the intubation tube and are configured to produce one or more additional signals indicative of the respiratory status of the patient.

In an embodiment, the one or more additional sensors include at least one of a carbon-dioxide sensor and a pressure sensor. In another embodiment, the ventilation system includes one or more electrodes, which are coupled to the distal end of the intubation tube and are configured to detect triggering of a phrenic nerve, which activates a diaphragm of the patient.

In some embodiments, the ventilation system includes one or more electrodes, which are coupled to the distal end of the intubation tube and are configured to apply a triggering signal to a phrenic nerve of the patient, and the processor is configured, based on at least the first and second signals, to apply the triggering signal, via the one or more electrodes, to the phrenic nerve. In other embodiments, the first position includes the distal end of the intubation tube and the second position includes the proximal end of the intubation tube.

There is additionally provided, in accordance with an embodiment of the present invention, a method that includes, inserting into a trachea of the patient, an intubation tube, for flowing oxygen-enriched humidified air (OHA) toward lungs of the patient and for evacuating exhaust air exhaled from the lungs. The intubation tube includes (i) a distal end, which is inserted into the trachea, and (ii) a proximal end, which is connected to one or more tubes for receiving the OHA and evacuating the exhaust air. A first signal indicative of a first micro-acceleration of the intubation tube at a first position, is received from a first microgravity sensor, which is coupled to the intubation tube at the first position. A second signal indicative of a second micro-acceleration of the intubation tube at a second position, is received from a second microgravity sensor, which is coupled to the intubation tube at the second position, which is different from the first position. The ventilation system is controlled to apply a ventilation scheme responsively to the first and second signals.

In some embodiments, the method includes receiving, from one or more additional sensors, one or more additional signals indicative of the respiratory status of the patient. In other embodiments, the one or more additional signals are indicative of at least one of: (a) a carbon-dioxide volume in the exhaust air exhaled from the lungs, and (b) a pressure of at least one of (i) the exhaust air exhaled from the lungs, and (ii) the OHA flowing toward the lungs.

There is further provided, in accordance with another embodiment of the present invention, a method for producing a ventilator system for a patient, the method includes, receiving an intubation tube, which is configured to flow oxygen-enriched humidified air (OHA) toward lungs of the patient and to evacuate exhaust air exhaled from the lungs, the intubation tube including: (i) a distal end, configured to be inserted into a trachea of the patient, and (ii) a proximal end, configured to be connected to one or more tubes for receiving the OHA and evacuating the exhaust air. A first microgravity sensor is coupled to the intubation tube at a first position, for producing a first signal indicative of a first micro-acceleration of the intubation tube at the first position. A second microgravity sensor is coupled to the intubation tube at a second position, different from the first position, for producing a second signal indicative of a second micro-acceleration of the intubation tube at the second position. A processor, for controlling the ventilation system to apply a ventilation scheme responsively to the first and second signals, is connected to the first and second microgravity sensors.

The present invention will be more fully understood from the following detailed description of the embodiments thereof, taken together with the drawings in which:

DETAILED DESCRIPTION OF EMBODIMENTS

Overview

Ventilation systems are used for mechanically assisting or replacing autonomic breathing when a patient cannot breathe by himself/herself adequately. Such systems may be operated in different ventilation modes in accordance with the clinical situation of the patient as will be described below. In practice, when a patient attempts to breath, it is important not to resist such breathing attempts. For example, when the ventilation system supplies air and the patient coughs, the ventilator should be controlled to hold the air supply, and resume after the patient stops coughing and/or needs ventilation. Therefore, it is important to identify or even predict when the patient is trying, or will soon be trying, to breathe independently.

Embodiments of the present invention that are described hereinbelow provide improved techniques for estimating the respiratory status of a patient, so as to adjust a ventilation treatment responsively to the clinical condition of the patient, and particularly to changes in the respiratory ability of the patient.

In some embodiments, ventilator system for ventilating a patient comprises an intubation tube, which is configured to flow oxygen-enriched humidified air (OHA) toward lungs of the patient and to evacuate exhaust air exhaled from the lungs. The OHA is produced by the ventilation system and various parameters of the OHA, such as flow, pressure and gas mixture, are controlled by a processor of a control unit of the ventilator system.

In some embodiments, the intubation tube comprises (i) a distal end, configured to be inserted into the patient trachea, and (ii) a proximal end, configured to be connected to one or more tubes for receiving the OHA and evacuating the exhaust air.

In some embodiments, the ventilator system comprises a first microgravity sensor, coupled to the proximal end of the intubation tube, and configured to produce a first signal, also referred to herein as a first microgravity signal, indicative of a first micro-acceleration of the intubation tube at the proximal end. The ventilator system further comprises a second microgravity sensor, coupled to the distal end of the intubation tube, and configured to produce a second signal, also referred to herein as a second microgravity signal, indicative of a second micro-acceleration of the intubation tube at the distal end of the intubation tube.

The microgravity sensors are configured to detect small movements of the intubation tube, and therefore, the microgravity signals received by the processor may have insufficient signal-to-noise ratio for detecting or predicting changes in the respiratory status of the patient. In some embodiments, the processor is configured to calculate, based on the first and second microgravity signals, a differential signal for estimating the respiratory status of the patient. For example, the processor may calculate the differential signal by subtracting between the first and second microgravity signals.

In some embodiments, the ventilator system comprises one or more additional sensors, such as but not limited to a carbon-dioxide sensor and a pressure sensor, which are coupled to the distal end of the intubation tube. The carbon-dioxide sensor is configured for detecting the amount of carbon-dioxide flowing out of the patient lungs, and the pressure sensor is configured for sensing the pressure of the OHA and exhaust air flowing between the lungs and the intubation system. The ventilator system further comprises one or more electrodes, which are coupled to the distal end of the intubation tube and are configured to detect triggering of a phrenic nerve, which activates a diaphragm of the patient.

In some embodiments, based on the signals received from the sensors coupled to the intubation tube, the processor is configured to apply to the phrenic nerve, via the one or more electrodes, a triggering signal for stimulating self-respiratory of the patient.

The disclosed techniques improve the ventilation quality of a patient that cannot breathe by himself/herself, based on the differential signals derived from the microgravity signals received from sensors positioned at different location along the intubation tube. Such differential signals may be indicative of muscle contraction in the patient chest and/or in the patient diaphragm, which may indicate or even predict a change in the patient's state of consciousness. Such indications may be used by the control unit of the ventilation system for adapting the ventilation scheme to the respiratory status of the patient, so as to improve the treatment of such patients.

System Description

Figure 1:
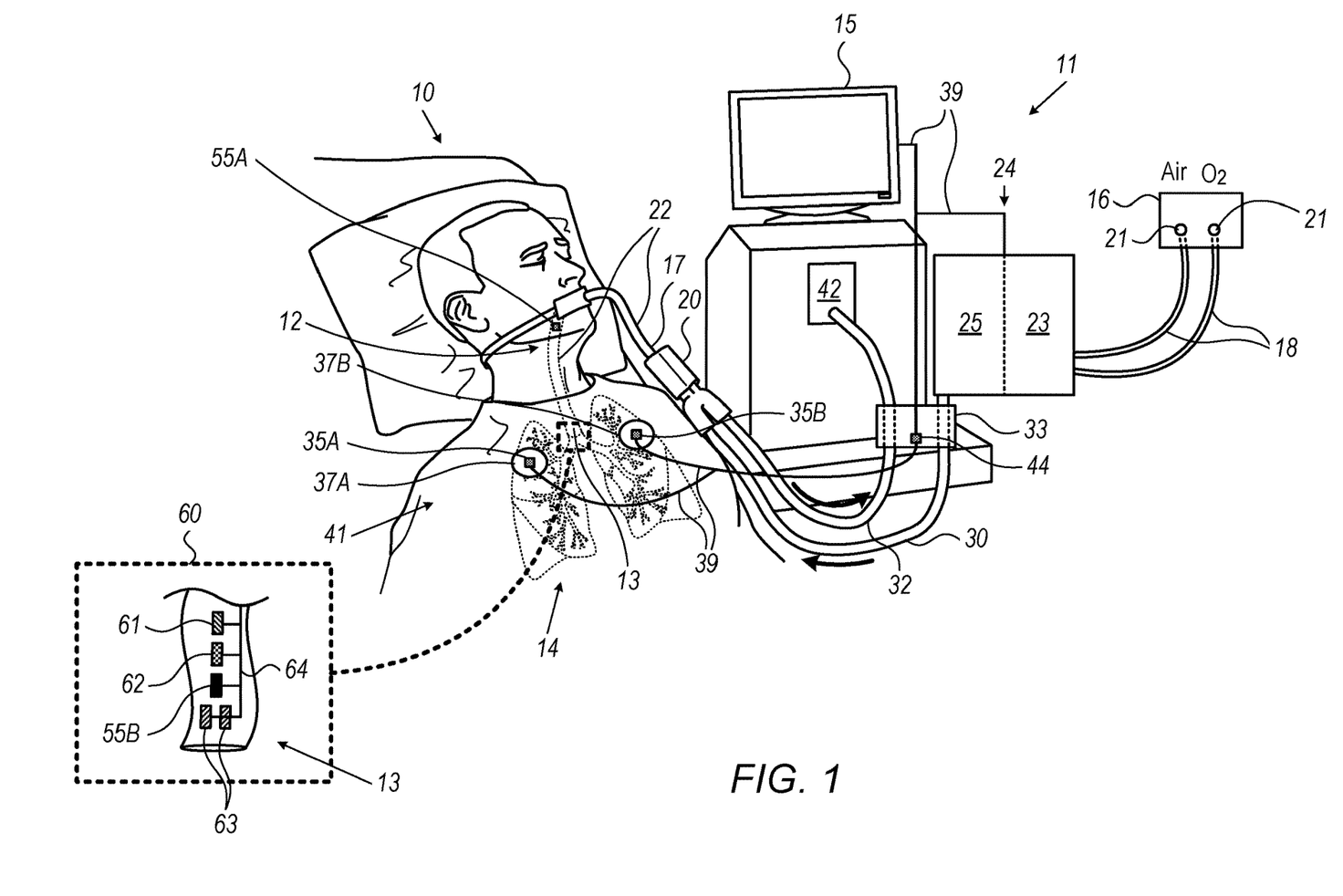
FIG. 1 is a schematic, pictorial illustration of a ventilation system having a subsystem for detecting respiratory status of a patient, in accordance with an embodiment of the present invention.

FIG. 1 is a schematic, pictorial illustration of a ventilation system 11, in accordance with an embodiment of the present invention.

In some embodiments, ventilation system 11 comprises an oxygen-enriched humidified air (OHA) supply subsystem (OHAS) 24 comprising an air compressor 23 and a humidifier 25. Air compressor 23 is configured to compress a preassigned gas mixture to a preassigned pressure described below.

In some embodiments, ventilation system 11 comprises tubes 18 connected between OHAS 24 and a hospital supply 16. In the present example, air compressor 23 is configured to receive, via outlets 21 of hospital supply 16, oxygen ($O_2$) and air so as to produce the aforementioned OHA at a preassigned mixture (e.g., defined in volumetric percentage) and a preassigned pressure. In the present example, the produced OHA has a typical percentage of oxygen between about 21% and 100% and a preassigned pressure between about zero $CmH_2O$ (when a patient 10 is self-breathing) and 50 $CmH_2O$.

In some embodiments, humidifier 25 is configured to harvest moisture from the environment or to receive water from any suitable source, so as to set a preassigned humidity of the OHA. For example, humidifier 25 is configured to supply OHA at a selected humidity level between about 40% and 100%, or at any other suitable humidity. In the present example, OHAS 24 comprises reusable air compressor 23 and humidifier 25, which may have to undergo a minimal or no cleaning or sterilization between ventilations of different patients 10.

In some embodiments, system 11 comprises an intubation tube 22 having a distal end 13, which is configured to be inserted into a trachea 12 of patient 10, and a proximal end 17, which is connected to a bifurcation adaptor 20.

In some embodiments, intubation tube 22 has a microgravity sensor 55A, which is coupled to proximal end 17 at any suitable position. In the example of FIG. 1, microgravity sensor 55A is positioned within the oral cavity of patient 10, but in other embodiments, microgravity sensor 55A may be positioned at any other suitable position along intubation tube 22, e.g., external to the oral cavity of patient 10 at proximal end 17, or within trachea 12 but not at distal end 13.

Reference is now made to an inset 60 showing distal end 13 of intubation tube 22. In some embodiments, intubation tube 22 comprises one or more types of sensors coupled to distal end 13. In the present example, (i) a carbon-dioxide (CO2) sensor 61, which is configured to produce a signal indicative of an amount (e.g., flow or pressure) of $CO_2$ exhaled or outflows from lungs 14 of patient 10, and (ii) a pressure sensor 62, which is configured to produce a signal indicative of the pressure of gases flowing between lungs 14 and intubation tube 22. Note that when system 11 inflows OHA into lungs 14, the signal produced by pressure sensor 62 provides an indication of the actual OHA pressure delivered into lungs 14. Similarly, when air flows from lungs 14 to intubation tube 22, pressure sensor 62 is configured to provide an indication of the actual pressure of air flowing out of lungs 14, and CO2 sensor 61 provides an indication of the amount of or the percentage of $CO_2$ (from the total volume of air) flowing out of lungs 14.

In some embodiments, intubation tube 22 comprises a microgravity sensor 55B, which may be similar to or different from microgravity sensor 55A described above, and is coupled to distal end 13 of intubation tube 22.

In some embodiments, microgravity sensors 55A and 55B are configured to produce first and second microgravity signals, respectively, also referred to herein as first and second signals, respectively. The first microgravity signal is indicative of a first micro-acceleration of intubation tube 22 at the position of microgravity sensor 55A, e.g., at proximal end 17. The second microgravity signal is indicative of a second micro-acceleration of intubation tube 22 at the position of microgravity sensor 55B, e.g., at distal end 13.

In some embodiments, microgravity sensors 55A and 55B comprise any suitable type of microgravity sensors. For example, LIS3DSHTR microgravity sensing family of products produced by STMicroelectronics (Geneva, Switzerland). In such embodiments, microgravity sensors 55A and 55B comprise digital micro-acceleration sensors configured to sense three-dimensional micro-acceleration with acceleration range of about ±2 g, 4 g, 6 g, 8 g, 16 g and a sensing sensitivity ranges between about 16666 (±2 g) LSB/g and 1369 (±16 g) LSB/g. In other words, the sensitivity of LIS3DSHTR-based microgravity sensors 55A and 55B is about 120 micro-g, which corresponds to 16666 (±2 g) LSB/g. As described above, microgravity sensors 55A and 55B may comprise the same product of microgravity sensor or different products, and may comprise any suitable type of microgravity sensor other than the aforementioned LIS3DSHTR microgravity sensing family of products.

In some embodiments, intubation tube 22 comprises one or more electrodes 63, in the present example two electrodes 63, which are coupled to distal end 13 and are configured to detect triggering of a phrenic nerve (not shown), which activates the diaphragm (not shown) of patient 10. Additionally or alternatively, electrodes 63 are configured to apply a triggering signal to the phrenic nerve of patient 10.

In some embodiments, intubation tube 22 comprises a braid 64 of electrical leads, such as electrical wires or electrical traces formed on a flexible printing circuit (not shown), which are configured to electrically connect between (i) sensors 61, 62, 55A and 55B and electrodes 63, and (ii) a control unit 33 of system 11, which is described in detail below.

In other embodiments, instead of braid 64, system 11 comprises one or more wireless communication devices (not shown), which are coupled to intubation tube 22, and additional one or more wireless communication devices (not shown) integrated in control unit 33. The wireless communication devices (WCDs) and the additional WCDs are configured to exchange the sensed and triggering signals wirelessly instead of via braid 64. In such embodiments, the configuration of system 11 may exclude braid 64 and comprise the WCDs.

Reference is now made back to the general view of FIG. 1. In some embodiments, ventilation system 11 comprises an OHA tube 30, which is coupled between bifurcation adaptor 20 and OHAS 24, and is configured to flow the OHA produced by air compressor 23 and humidifier 25 or OHAS 24, via intubation tube 22, toward lungs 14 of patient 10. Note that lungs 14 are exposed by depiction in FIG. 1 and shown for the sake of more clear presentation, noting that lungs 14 in the thoracic cavity of the patient 10 which is covered with natural tissue (e.g., pleura, bone, muscles, skin, etc.) removed from FIG. 1 for the sake of conceptual clarity.

In some embodiments, system 11 further comprises an exhaust tube 32, which is coupled between bifurcation adaptor 20 and an air evacuation system (AES) 42 of the hospital. Exhaust tube 32 is configured to flow exhaust air exhaled from lungs 14, via intubation tube 22, toward AES 42.

Note that the term "exhaled" is applicable when patient 10 can independently exhale at least a portion of the air from lungs 14. Otherwise, the term exhaled may be replaced with the terms "evacuated", "aspirated" or "sucked" referring to evacuation, aspiration or suctioning, typically part of the air, from lungs 14 of patient 10.

In other embodiments, ventilation system 11 comprises multiple patches, in the present example, two patches 37A and 37B coupled externally, e.g., to the skin, of a chest 41 of patient 10. Each patch comprises one or more electrodes, in the present example, patch 37A comprises an electrode 35A and patch 37B comprises an electrode 35B.

In some embodiments, electrode 35A is configured to produce a first electrocardiogram (ECG) signal, and electrode 35B is configured to produce a second ECG signal.

In some embodiments, control unit 33 of ventilation system 11 is configured to monitor and control parameters of the ventilation process, such as but not limited to the ventilation rate, gas mixture (e.g., oxygen), flow rate (e.g., between about 10 liter per minute (LPM) and 60 LPM, or at any other suitable flow rate) and the humidity of the OHA flowing into lungs 14. In the present example, control unit 33 comprises a processor 44, which is electrically connected via electrical leads 39 (or suitable cables), inter-alia, to OHAS 24, a display 15, electrodes 35A and 35B and additional devices such as sensors and valves (not shown) for controlling ventilation system 11.

In some embodiments, braid 64 of the electrical leads is connected to control unit 33 (e.g., by having the electrical leads coupled to and running along intubation tube 22 and exhaust 32) and configured to exchange signals between processor 44 and the devices (e.g., sensors 61, 62, 55A and 55B and electrodes 63 described above) that are coupled to intubation tube 22.

In some embodiments, processor 44 is configured to control air compressor 23 and humidifier 25 of OHAS 24, by setting the preassigned thresholds, such as gas mixture (having oxygen percentage between about 21% and 100%), pressure (between about 0 $CmH_2O$ and 100 $CmH_2O$) and humidity (e.g., between about 40% and 100%) of the OHA, and by controlling the frequency of the ventilation rate carried out by compressor 23.

In some embodiments, system 11 comprises one or more displays, such as but not limited to display 15 or a display (not shown) of control unit 33.

In some embodiments, processor 44 is configured to display, e.g., on display 15, one or more parameters indicative of the ventilation rate, flow rate, and/or humidity and/or any other suitable parameter of the OHA as well as the exhaust air flowing in tubes 30 and 32 as described above.

In some embodiments, processor 44 is configured to control ventilation system 11 to apply a ventilation scheme responsively to the first and second microgravity signals received from microgravity sensors 55A and 55B.

In some embodiments, processor 44 is configured to estimate the respiratory status of patient 10 based on the first and second microgravity signals. For example, processor 44 is configured to calculate, based on the first and second microgravity signals, a differential signal for estimating the respiratory status of patient 10. The differential signal may be produced by processor 44 using any suitable technique, for example, by subtracting between the first and second microgravity signals.

In some embodiments, processor 44 is configured to control ventilation system 11 to apply the ventilation scheme depending on the estimated respiratory status, which is based on the differential signal. Note that by using the differential signal, processor 44 improves the sensitivity for detecting whether patient 10 is self-breathing because global movements of patient 10 (where both microgravity sensors 55A and 55B are moving together) will be excluded from the differential signal. For example, when the patient goes from an unconscious or anesthesia to a conscious state, he or she may move the body or at least some organs, so that using a differential signal may sort out moves that are not directly related to the respiratory status of patient 10.

In such embodiments, processor 44 is configured to identify any relative movement between the first and second microgravity signals sensed by microgravity sensors 55A and 55B, respectively. For example, when patient 10 starts inhaling air, microgravity sensor 55A moves relative to microgravity sensor 55B (because the muscles in the oral cavity of patient 10 are moving), and subsequently, microgravity sensor 55B moves relative to microgravity sensor 55A when lungs 14 are inflated to some extent, and are moving microgravity sensor 55B relative to microgravity sensor 55A. Similarly, when patient 10 starts exhaling air, microgravity sensor 55B moves relative to microgravity sensor 55A, and subsequently, microgravity sensor 55A moves relative to microgravity sensor 55B. In such embodiments, processor 44 is configured to control OHAS 24 to reduce the pressure and/or flow rate of OHA flowing into lungs 14, so as to assist and/or stimulate the self-respiratory of patient 10.

In some embodiments, based on the differential signals produced by subtracting between the first and second microgravity signals, processor 44 is configured to detect when patient 10, intends to stop and/or gradually stops and/or immediately stops, the self-respiratory. In such embodiments, processor 44 is configured to control OHAS 24 to increase the flow rate and/or pressure of the OHA flowing, through intubation tube 22, into lungs 14. In some embodiments, in addition to the ventilation scheme adjustment based on the differential signal, processor 44 is further configured to tune the adjustment of the ventilation scheme responsively to the ECG signals received from electrodes 35A and 35B.

In some embodiments, in addition to the ventilation scheme adjustment based on the differential signal, processor 44 is further configured to tune the adjustment of the ventilation scheme responsively to the signals received from $CO_2$ sensor 61 and/or pressure sensor 62.

In some embodiments, based on the respiratory status of patient 10 and/or the ventilation scheme applied to patient 10, processor 44 is configured to apply electrodes 63 for stimulating the self-respiratory of patient 10, by triggering the phrenic nerve. Additionally or alternatively, processor 44 may tune the ventilation adjustment based on signals received from one or more electrodes 63 detecting the triggering of the phrenic nerve, in addition to the differential signal that may be indicative of movement of the diaphragm of patient 10.

Additionally or alternatively, based on the first and second ECG signals received from electrodes 35A and 35B, respectively, processor 44 is configured to control ventilation system 11 to apply a ventilation scheme or mode responsively to the ECG signals received from electrodes 35A and 35B. Such techniques are described in detail, for example, in U.S. Provisional Patent Application 63/107,009, whose disclosure is incorporated herein by reference.

In some embodiments, processor 44 is configured to adjust the ventilation rate (i.e., the number of ventilation cycles per minute) and other ventilation parameters responsively to the signals received from microgravity sensors 55A and 55B, and from sensors 61 and 62, and from electrodes 63, 35A and 35B. For example, when the initial differential signal (derived from the first and second differential signals) is indicative of unconsciousness or anesthesia and a later differential signal indicates or predicts that patient 10 is regaining consciousness, processor 44 may adjust one or more ventilation parameters, such as the ventilation rate of the OHA supplied by compressor 23 of OHAS 24.

In such embodiments, processor 44 is configured to switch between a hyper-ventilation mode (HVM) and a normal-ventilation mode (NVM) of ventilation system 11. In other words, based on the differential signal, processor 44 is configured to detect or even predict that patient 10 is regaining consciousness, and therefore may reduce the ventilation rate from about 100 ventilation cycles per minute to about 15 ventilation cycles per minute.

In the context of the present disclosure and in the claims, the terms "about" or "approximately" for any numerical values or ranges indicate a suitable dimensional tolerance that allows the part or collection of components to function for its intended purpose as described herein.

In some embodiments, processor 44 is configured to switch between the HVM and NVM modes by controlling the frequency at which air compressor 23 and humidifier 25 of OHAS 24 are producing the specified attributes of the OHA produced by OHAS 24.

Typically, processor 44 comprises a general-purpose processor, which is programmed in software to carry out the functions described herein. The software may be downloaded to the processor in electronic form, over a network, for example, or it may, alternatively or additionally, be provided and/or stored on non-transitory tangible media, such as magnetic, optical, or electronic memory.

This particular configuration of ventilation system 11 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example system, and the principles described herein may similarly be applied to other sorts of ventilation systems and/or to any other sorts of ventilation subsystems used, for example, as modules of a system for conducting any medical procedure.

Figure 2:
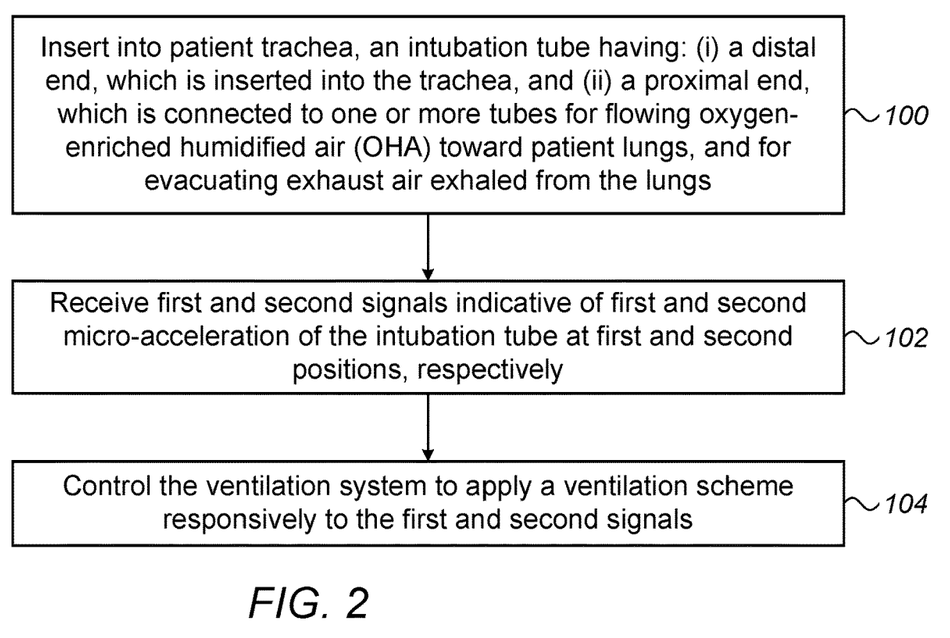
FIG. 2 is a flow chart that schematically illustrates a method for controlling ventilation based on signals received from sensors coupled to an intubation tube, in accordance with an embodiment of the present invention.

Controlling Ventilation Using Differential Microgravity Signal for Estimating Patient Respiratory Status FIG. 2 is a flow chart that schematically illustrates a method for controlling ventilation based on signals received from sensors coupled to an intubation tube, in accordance with an embodiment of the present invention.

The method begins at an intubation tube insertion step 100, with inserting into trachea 12, intubation tube 22 having: (i) distal end 13, which is inserted into the trachea and has sensors 55B, 61, and 62 and electrodes 63 coupled thereto, and (ii) proximal end 17, which is connected, via adaptor 20, to tubes 30 and 32 for flowing OHA toward lungs 14, and for evacuating exhaust air exhaled from lungs 14, as described in detail in FIG. 1 above.

At a microgravity signals receiving step 102, processor 44 receives from microgravity sensors 55A and 55B, first and second microgravity signals indicative of first and second micro-acceleration of intubation tube 22, the first and second microgravity signals are acquired at the proximal and distal ends of intubation tube 22, respectively, as described in detail in FIG. 1 above.

In some embodiments, processor 44 produces the differential signal based on the first and second microgravity signals, as described in detail in FIG. 1 above.

At a ventilation system controlling step 104 that concludes the method, processor 44 estimated the respiratory status of patient 10 and controls ventilation system 11 to apply or adjust the ventilation scheme responsively to the differential signal, which is based on the first and second microgravity signals. As described in FIG. 1 above, processor 44 may use additional signals received from any of sensors 61 and 62, and from any of electrodes 63, 35A and 35B, for further tuning the ventilation scheme. Moreover, processor 44 may apply triggering signals, via electrodes 63, to the phrenic nerve for stimulating the self-respiratory of patient 10, as described in detail in FIG. 1 above.

This particular method of FIG. 2 is shown by way of example, in order to illustrate certain problems that are addressed by embodiments of the present invention and to demonstrate the application of these embodiments in enhancing the performance of such a ventilation method. Embodiments of the present invention, however, are by no means limited to this specific sort of example method, and the principles described herein may similarly be applied to other sorts of ventilation systems and/or to any other sorts of methods for ventilating patients.

Figure 3:
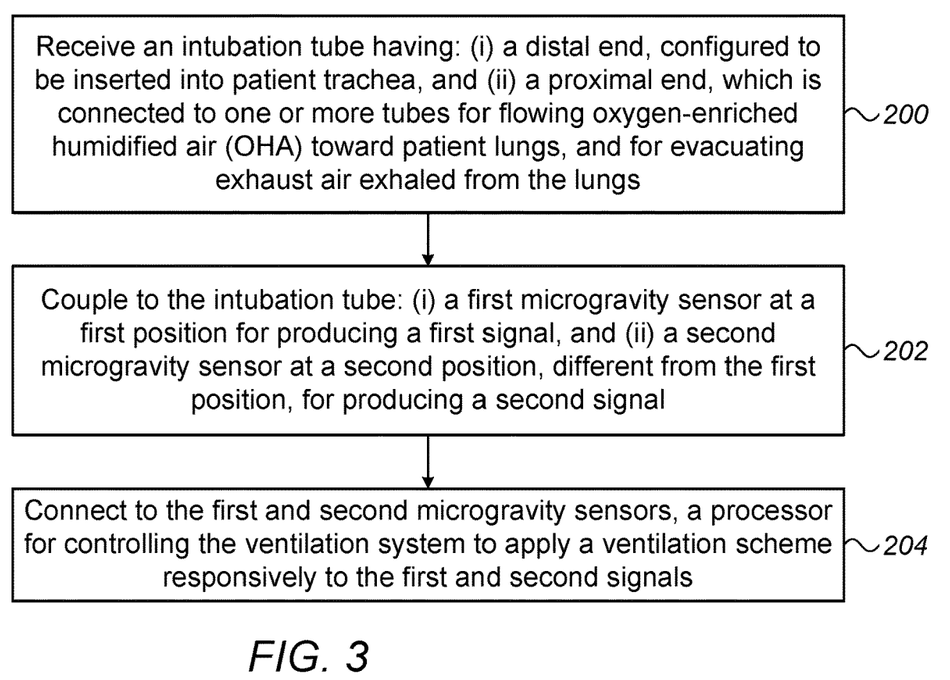
FIG. 3 is a flow chart that schematically illustrates a method for producing a ventilation system, in accordance with an embodiment of the present invention.

FIG. 3 is a flow chart that schematically illustrates a method for producing ventilation system 11, in accordance with an embodiment of the present invention.

The method begins at an intubation tube receiving step 200, with receiving intubation tube 22 having (i) distal end 13, configured to be inserted into patient trachea 12, and (ii) proximal end 17, which is connected, via adaptor 20, to tubes 30 and 32 for flowing OHA toward lungs 14, and for evacuating exhaust air exhaled from lungs 14, as described in detail in FIG. 1 above.

In other embodiments, the method further comprises connecting proximal end 17 to one or more tubes, such as tubes 30 and 32, using adaptor 20 or any other suitable coupling technique.

At a device coupling step 202, microgravity sensor 55A is coupled to proximal end 17 for producing the first microgravity signal indicative of the first micro-acceleration of intubation tube 22 at proximal end 17. Moreover, microgravity sensor 55B is coupled to distal end 13 for producing the second microgravity signal indicative of the second micro-acceleration of intubation tube 22 at distal end 13.

In some embodiments, the one or more WCDs described in FIG. 1 above may also be coupled to distal end 13, and the additional one or more WCDs may be coupled to proximal end 17 for exchanging the signals between (i) the aforementioned sensors and electrodes coupled to intubation tube, and (ii) processor 44 of control unit 33.

At a devices connecting step 204 that concludes the method, braid 64 of the electrical leads and/or the WCDs described in FIG. 1 and step 202 above, are used for connecting between: (i) microgravity sensors 55A and 55B (and between sensors 61 and 62 and electrodes 63) and (ii) processor 44 of control unit 33, as described in FIG. 1 above. In some embodiments, the connection between the devices of step 202 and processor 44 is carried out for controlling the ventilation system to apply and/or adjust the aforementioned ventilation scheme responsively to the first and second microgravity signals, as well as the other sensed signals received from sensors 61 and 62 and from electrodes 63. The electrical connection may also be used for applying the triggering signals, via electrodes 63, to the phrenic nerve for stimulating the self-respiratory of patient 10.

In other embodiments, the connection between proximal end 17 and the one or more tubes, which is described in step 200 above, may be carried out after concluding the coupling and connecting of the devices described in steps 202 and 204 above.

This particular method for producing system 11 is shown by way of example, in order to illustrate certain problems that are addressed by embodiments of the present invention and to demonstrate the application of these embodiments in enhancing the performance of such a system. Embodiments of the present invention, however, are simplified for the sake of conceptual clarity and are by no means limited to this specific sort of example method for producing this ventilation system. Moreover, it will be understood that the production of such ventilation systems comprises additional steps intentionally omitted from the method for the sake of simplicity of the presentation.

Although the embodiments described herein mainly address ventilator system for a patient, the methods and systems described herein can also be used in other applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A ventilator system for a patient, the ventilator system comprising:
    an intubation tube, configured to flow oxygen-enriched humidified air (OHA) toward lungs of the patient and to evacuate exhaust air exhaled from the lungs, the intubation tube comprising: (i) a distal end, configured to be inserted into a trachea of the patient, and (ii) a proximal end, configured to be connected to one or more tubes for receiving the OHA and evacuating the exhaust air;
    a first microgravity sensor, coupled to the intubation tube at a first position, and configured to produce a first signal indicative of a first micro-acceleration of the intubation tube at the first position;
    a second microgravity sensor, coupled to the intubation tube at a second position, different from the first position, and configured to produce a second signal indicative of a second micro-acceleration of the intubation tube at the second position; and
    a processor, which is configured to control the ventilation system to apply a ventilation scheme responsively to the first and second signals.

2. The ventilator system according to claim 1, wherein the processor is configured to estimate a respiratory status of the patient based on the first and second signals, and to control the ventilation system to apply the ventilation scheme depending on the estimated respiratory status.

3. The ventilator system according to claim 2, wherein the processor is configured to calculate, based on the first and second signals, a differential signal for estimating the respiratory status of the patient.

4. The ventilator system according to claim 2, and comprising one or more additional sensors, which are coupled to the intubation tube and are configured to produce one or more additional signals indicative of the respiratory status of the patient.

5. The ventilator system according to claim 4, wherein the one or more additional sensors comprise at least one of a carbon-dioxide sensor and a pressure sensor.

6. The ventilator system according to claim 1, and comprising one or more electrodes, which are coupled to the distal end of the intubation tube and are configured to detect triggering of a phrenic nerve, which activates a diaphragm of the patient.

7. The ventilator system according to claim 1, and comprising one or more electrodes, which are coupled to the distal end of the intubation tube and are configured to apply a triggering signal to a phrenic nerve of the patient, and wherein the processor is configured, based on at least the first and second signals, to apply the triggering signal, via the one or more electrodes, to the phrenic nerve.

8. The ventilator system according to claim 1, wherein the first position comprises the distal end of the intubation tube and the second position comprises the proximal end of the intubation tube.

9. A method, comprising:
    inserting into a trachea of a patient, an intubation tube, for flowing oxygen-enriched humidified air (OHA) toward lungs of the patient and for evacuating exhaust air exhaled from the lungs, the intubation tube comprising: (i) a distal end, which is inserted into the trachea, and (ii) a proximal end, which is connected to one or more tubes for receiving the OHA and evacuating the exhaust air;
    receiving, from a first microgravity sensor, which is coupled to the intubation tube at a first position, a first signal indicative of a first micro-acceleration of the intubation tube at the first position;
    receiving, from a second microgravity sensor, which is coupled to the intubation tube at a second position, different from the first position, a second signal indicative of a second micro-acceleration of the intubation tube at the second position; and
    controlling a ventilation system to apply a ventilation scheme responsively to the first and second signals.

10. The method according to claim 9, wherein controlling the ventilation system comprises estimating a respiratory status of the patient based on the first and second signals, and controlling the ventilation system to apply the ventilation scheme depending on the estimated respiratory status.

11. The method according to claim 10, wherein estimating the respiratory status comprises calculating, based on the first and second signals, a differential signal, and controlling the ventilation system to apply the ventilation scheme depending on the differential signal.

12. The method according to claim 10, and comprising receiving, from one or more additional sensors, one or more additional signals indicative of the respiratory status of the patient.

13. The method according to claim 12, wherein the one or more additional signals are indicative of at least one of: (a) a carbon-dioxide volume in the exhaust air exhaled from the lungs, and (b) a pressure of at least one of (i) the exhaust air exhaled from the lungs, and (ii) the OHA flowing toward the lungs.

14. The method according to claim 9, and comprising detecting triggering of a phrenic nerve of the patient, which activates a diaphragm of the patient.

15. The method according to claim 9, and comprising applying a triggering signal to a phrenic nerve of the patient, using one or more electrodes coupled to the distal end of the intubation tube.

16. The method according to claim 9, wherein the first position comprises the distal end of the intubation tube and the second position comprises the proximal end of the intubation tube.

17. A method for producing a ventilator system for a patient, the method comprising:
    receiving an intubation tube, which is configured to flow oxygen-enriched humidified air (OHA) toward lungs of the patient and to evacuate exhaust air exhaled from the lungs, the intubation tube comprising: (i) a distal end, configured to be inserted into a trachea of the patient, and (ii) a proximal end, configured to be connected to one or more tubes for receiving the OHA and evacuating the exhaust air;
    coupling to the intubation tube: (i) a first microgravity sensor at a first position for producing a first signal indicative of a first micro-acceleration of the intubation tube at the first position, and (ii) a second microgravity sensor at a second position, different from the first position, for producing a second signal indicative of a second micro-acceleration of the intubation tube at the second position; and connecting, to the first and second microgravity sensors, a processor for controlling the ventilation system to apply a ventilation scheme responsively to the first and second signals.

18. The method according to claim 17, and comprising, coupling to the intubation tube, one or more additional sensors for producing one or more additional signals indicative of a respiratory status of the patient.

19. The method according to claim 18, wherein the one or more additional sensors comprise at least one of a carbon-dioxide sensor and a pressure sensor.

20. The method according to claim 17, and comprising, coupling to the distal end of the intubation tube, one or more electrodes for at least one of: (i) detecting triggering of a phrenic nerve of the patient, which activates a diaphragm of the patient, and (ii) applying a triggering signal to the phrenic nerve.

* * * * *